(12) United States Patent
Prabhakarpandian et al.

(10) Patent No.: US 8,417,465 B2
(45) Date of Patent: *Apr. 9, 2013

(54) SYNTHETIC MICROFLUIDIC BLOOD-BRAIN BARRIER

(75) Inventors: Balabhaskar Prabhakarpandian, Madison, AL (US); Kapil Pant, Madison, AL (US); Shivshankar Sundaram, Tampa, FL (US); Ketan Harendrakumar Bhatt, Madison, AL (US)

(73) Assignee: CFD Research Corporation, Huntsville, AL (US)

( * ) Notice: Subject to any disclaimer, the term of this patent is extended or adjusted under 35 U.S.C. 154(b) by 486 days.

This patent is subject to a terminal disclaimer.

(21) Appl. No.: 12/726,140

(22) Filed: Mar. 17, 2010

(65) Prior Publication Data

US 2011/0104658 A1    May 5, 2011

Related U.S. Application Data

(63) Continuation-in-part of application No. 12/612,573, filed on Nov. 4, 2009.

(51) Int. Cl.
*G01N 33/48*    (2006.01)

(52) U.S. Cl. .......................................................... 702/19
(58) Field of Classification Search ..................... 702/19
See application file for complete search history.

(56) References Cited

U.S. PATENT DOCUMENTS

2006/0154361 A1 *   7/2006   Wikswo et al. ............ 435/289.1

OTHER PUBLICATIONS

Dickerson et al. "Limited Adhesion of Biodegradable Microspheres to E- and P- Selectin Under Flow," Biotechnology and Bioengineering (2001) vol. 73, issue 6, pp. 500-509).*
Shevkoplyas et al. Microvascular Research (2003) 65:132-136.
Weigle et al. "Lab-on-a-chip for drug development" Advanced Drug Delivery Reviews 55:349-377 (2003).
Long et al. "Numerical study of blood flow in an anatomically realistic aorto-iliac bifurcation generated from MRI data" Magnetic Resonance in Medicine 43(4):565-76 (2000) Abstract.

* cited by examiner

*Primary Examiner* — Jerry Lin
(74) *Attorney, Agent, or Firm* — Maschoff Brennan

(57) ABSTRACT

An apparatus and method for assaying blood-brain barrier properties for drug and drug delivery vehicle screening comprising of a microfluidic apparatus with gaps separating lumen and tissue space enabling formation of tight junctions similar to in vivo conditions using endothelial cells and brain cells.

31 Claims, 11 Drawing Sheets

Symmetric Diameter, Symmetric Angle

Symmetric Diameter, Asymmetric Angle

Asymmetric Diameter, Symmetric Angle

US 8,417,465 B2

SYNTHETIC MICROFLUIDIC BLOOD-BRAIN BARRIER

CROSS-REFERENCE TO RELATED APPLICATIONS

This application claims priority under 35 U.S.C. 120 to application Ser. No. 12/612,573 filed Nov. 4, 2009, which is incorporated by reference.

STATEMENT REGARDING FEDERALLY SPONSORED RESEARCH

The U.S. Government may have certain rights in this invention pursuant to Contact Number 1R43CA139841-01 awarded by the National Institutes of Health.

BACKGROUND OF THE INVENTION

1. Field of the Invention

The present invention relates to microfluidic devices and assay methods for selecting and optimizing the delivery of drugs across the blood-brain barrier.

2. Description of Related Art

Screening drug candidates and drug delivery vehicles for their abilities to cross from the blood into the brain through the Blood-Brain Barrier (BBB) is an important aspect of the development of Central Nervous System (CNS) therapeutics. Available in vitro BBB assays use incubation chambers separated by a filter membrane designed to mimic the BBB. Such devices do not reproduce physiological microenvironmental parameters, shear stress induced by blood flow and transport effects caused by phenotypic changes in the microvasculature. In vivo BBB assays involve small animal models that are expensive, lengthy and difficult to scale up for high throughput screening. Existing in vitro and in vitro BBB assays do not provide cost- and time-effective formats for real-time visualization or quantitation of the transport of drug and drug delivery candidates across the BBB.

The Synthetic Microvascular Blood-Brain Barrier (SyM-BBB) provides apparatus and methods for predicting drug and drug carrier transport across the BBB. In addition, it can be used to study dysfunction of the BBB following an insult (biological, chemical, mechanical or electrical). Interactions of cells under normal and pathological conditions with the BBB can also be visualized and quantitated in real-time.

Compared with static well-plate incubation assays as well as the other available in vitro platforms, the SyM-BBB accurately reproduces in vivo size and flow microenvironments and enables a physiologically-relevant testing system for drug screening and delivery experiments, as well as basic and applied research. Polymeric microfluidic technology (polydimethylsiloxane or PDMS) is used to create inexpensive, disposable chips. PDMS constructs can be used to realize long-term cell culture and cellular assays on these microfluidic chips. By bonding the polymer microchannel onto a custom glass bottom laid out in the appropriate form, the model also be readily extended onto standard 24 or 96 well plates, providing a ready method to scale up to high-throughput screening.

BRIEF SUMMARY OF THE INVENTION

The Synthetic Microvascular Blood-Brain Barrier (SyM-BBB) comprises a plastic, disposable and optically clear microfluidic chip with embedded microfluidic flow channels having geometric features and sizes similar to those found in vivo. The device comprises two sides/chambers: (1) an apical side/chamber in which endothelial cells (primary or immortalized) are grown, and (2) a basolateral side/chamber in which neuronal, glial and astrocytes (primary or immortalized) are grown or media conditioned with one or combination of the cells is located. Fluid within channels on the apical side is in liquid communication with one or more basolateral side tissue spaces via 0.2-5 µm gaps in the walls comprising repetitive, isolated structures or "islands," preferably embodied as posts or pillars.

The integrity and tightness of SyM-BBB can be probed either fluidically using permeability assays or electrically by measuring resistivity or complex impedance across the channel walls.

For permeability studies, tagged (e.g., fluorescently labeled) drug and/or drug delivery vehicle candidates are introduced into an apical side of the SyM-BBB. The movement of candidates from the flow channels through the layer(s) of cells and into the tissue space(s) is measured using one or more standard imaging techniques. The measured permeabilities of candidates may be used to objectively compare drugs in their ability to cross the BBB. In addition, disruption or changes in the integrity and tightness of the BBB can be measured.

Following an insult, inflammatory responses and interactions of cells (leukocytes, neurons, etc.) can be analyzed. Screening of therapeutics (e.g., drugs, stem cells) for restoration of normal conditions is also possible.

DETAILED DESCRIPTION OF THE INVENTION

Definitions

Figure 1:
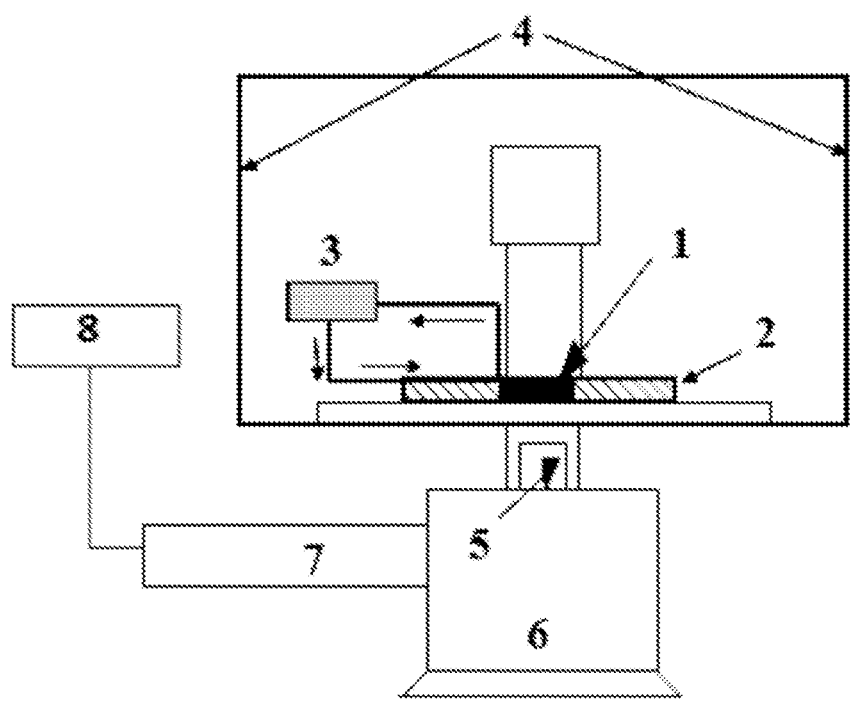
FIG. 1 is a drawing showing the components of a system used for measuring blood-brain barrier penetration.

A "synthetic microvascular network" (SMN) is a man made network comprising interconnected, nonlinear flow channels that form geometrical features and have fluid flow properties found in physiological microvascular networks of the brain. The flow channels (synthetic vessels) form intersecting networks and may be arranged end to end, analogous to an arteriole, capillary, venule sequence. Flow channels and the SMNs they form possess geometric characteristics of physiological microvascular including variable cross-sectional shapes, variable cross-sectional areas, convolutions, turns, and/or anastomoses. A network of linear channels joining at angles, for example, is not an SMN because such a network possesses geometrical shapes and produced flow characteristics not found in physiological microvascular networks. Straight channels or other channels having non-physiological geometries may be used to link a synthetic microvascular network to other components of a microfluidic chip. These channels, however, are not a part of the microvascular network. Flow channels in a SyM-BBB based on SMNs comprise of porous walls (0.2-5 µm) such that liquid may move from the apical (lumen) chamber into the basolateral chamber in a manner similar to the movement of fluid from the lumen of a physiological vessel into an interstitial space in the brain comprising of astrocytes, neurons, etc.

An Idealized microvascular network (IMN) is a man made network comprising interconnected flow channels that have certain fluid flow properties found in physiological microvascular networks. The diameters of the channels range from 10-500 µm and comprise of angles typically between 15° and 135°. Flow channels in a SyM-BBB based on IMNs comprise porous walls (0.2-5 µm) such that liquid may move from the apical chamber into the basolateral chamber in a manner similar to the movement of fluid from the lumen of a physiological vessel into an interstitial space.

As used herein, the term "idealized" in association with a microfluidic network, junction, or bifurcation is used to describe a synthetic network, junction, or bifurcation consisting of straight microfluidic channels joined at acute, right, or obtuse angles.

As used herein, a microfluidic channel may have a rectangular, circular, semi-circular, irregular or a combination of cross-sectional shapes. The dimensions of a channel are described, for example, by length, depth and width wherein the depth is measured perpendicular to the plane of a microfluidic chip containing the channel and length and width are measured in directions lying in the plane of the microfluidic chip containing the channel. Channels having circular or semi-circular cross-sections may be described as having variable depth and width relative to channels having rectangular cross-sections or may alternatively be described in terms of channel diameter. Maximum depth and width when used to describe a channel having a circular or semi-circular cross-section are both equal to the maximum diameter of the channel. When used to describe a channel having a rectangular cross-section, the maximum width and depth refer to the constant width and depth of a channel having a constant width and depth or to the highest values for width and depth for channels having variable width and depth.

A microfluidic chip is constructed using techniques employed in the semiconductor industry such as photolithography, wet chemical etching, thin film deposition and soft lithography using polymeric substrates, such as Polydimethylsiloxane (PDMS). Other materials that may be used in place of PDMS include Poly(Styrene Butadiene Styrene) (SBS) and Poly(Styrene-Ethylene-Butadiene-Styrene) (SEBS) elastomers, Polyester-ether (PEE) thermoplast, and thermoset polyester (TPE), which can be used for replica molding fabrication techniques. Polyolefin plastomer (POP's) can be specifically used for submicron range channels. Glass or quartz with reactive wet/dry etching of the microchannels can also be used. Thermoplastic materials such as polymethylmethacrylate (PMMA), polycarbonate (PC), cyclic olefin copolymer (COC), polystyrene (PS), poly vinyl chloride (PVC), and polyethylene terephthalate glycol (PETG) can be used with embossing techniques or injection molding. PS, PC, cellulose acetate, polyethylene terephthalate (PET), PMMA, PETG, PVC, PC, and polyimide can also be used with laser ablation techniques. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms.

"Tortuosity" is a measure of the indirectness of a vessel or flow channel path. Tortuosity can be measured in several ways. One exemplary means of measuring tortuosity is to sum the angles between consecutive trios of points along the space curve represented by a vessel skeleton and then normalize by path length. Tortuosity may also be measured, for example, by counting inflection points along each vessel or flow channel and multiplying this number (plus one) times the total path length and then dividing by the distance between the ends of the each vessel or flow path.

BBB Penetration Assay System:

FIG. 1 shows a non-limiting example of a system for performing blood-brain barrier (BBB) delivery assays according to the present invention. The system comprises a pumping means (3), such as a peristaltic pump (for recirculation/multiple pass) or a syringe pump (single pass), to move fluids through microfluidic channel networks in a microfluidic chip (1). For experiments with a peristaltic pump, the microfluidic chip (1) is placed on an automated stage device (2) and connected to a pumping means (3) that is connected to inlets, outlets, and, optionally, ports on the microfluidic chip (1). Alternatively, ports on the microfluidic chip (1) may be connected to a second pumping means (not shown). The microfluidic chip (1) is preferably contained within an incubation chamber (4) and is positioned over an objective lens (5) of a brightfield, phase contrast or fluorescent microscope (6). Optical means such as a CCD camera or video camera (7) are used for visualization within the microfluidic chip (1). A computer (8) is in communication with microscope (6), camera (7), and the microscope mounted accessories for data collection and control. For experiments with a syringe pump, the pump (3) is connected to the microfluidic chip (1) and fluid leaving the microfluidic chip (1) is sent to waste (not shown).

Figure 2:
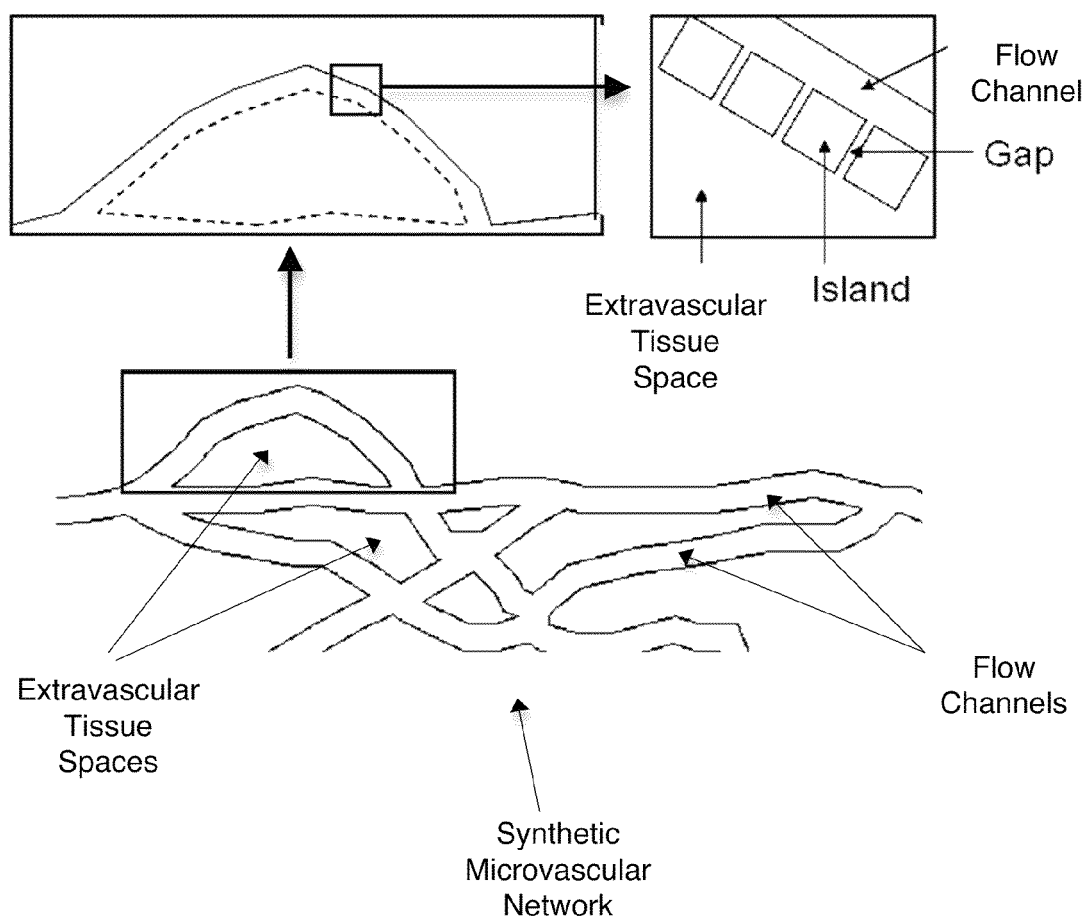
FIG. 2 is a drawing showing a SMN on a microfluidic chip.

Microfluidic Chips:

The microfluidic chips used in the assay system may comprise one or more SMNs, one or more IMNs, or a combination of SMNs and IMNs. FIG. 2 shows several views of a SMN in a microfluidic chip according to the invention. The SMN is made of interconnected nonlinear flow channels that form a geometry that provides flow conditions present in brain microvasculature, including convective flow and diffusion. The geometry of the SMN is identical to or derived from one or more images of one or more in-vivo brain microvascular networks. The SMN comprises one or more extravascular tissue spaces separated from the lumen (apical side) of flow channels by porous walls that allow liquid to diffuse from the flow channels into the tissue spaces. The tissue spaces preferably have cross-sectional luminal dimensions of between 100 µm and 1 cm and contain glial cells, astrocytes, neurons, astrocyte-conditioned media, or combinations thereof. The walls of flow channels surrounding the tissue spaces are constructed with 0.2-5 µm wide gaps to allow liquid diffusion. The gaps in the walls of the flow channels are openings located between structures or islands that form liquid permeable walls.

Figure 3:
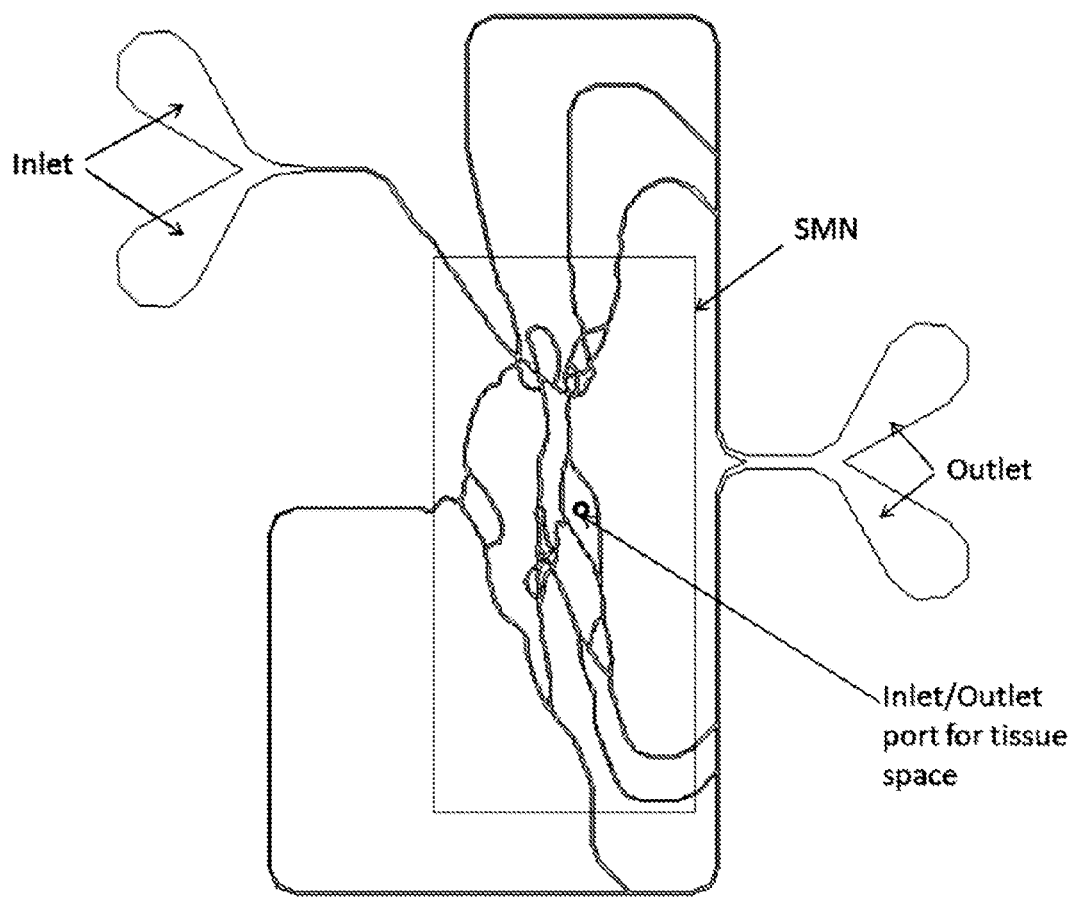
FIG. 3 is a drawing showing the components of a microfluidic chip for measuring blood-brain barrier penetration using a SMN.

FIG. 3 shows an example of a microfluidic chip comprising a SMN and one or more tissue spaces. The tissue space(s) in a SMN or an IMN comprise an inlet port and an outlet port for introducing cells and growth into and flowing cells and growth media out of the tissue space(s). The pressure inside each tissue space may be regulated through a dedicated pressure valve or controlling back pressure downstream of the tissue space outlet port. The nonlinear flow channels in the SMN are in fluid communication with an inlet and an outlet via microfluidic channels. The location of tissue space(s) in a given network may be selected by the user.

Figure 4:
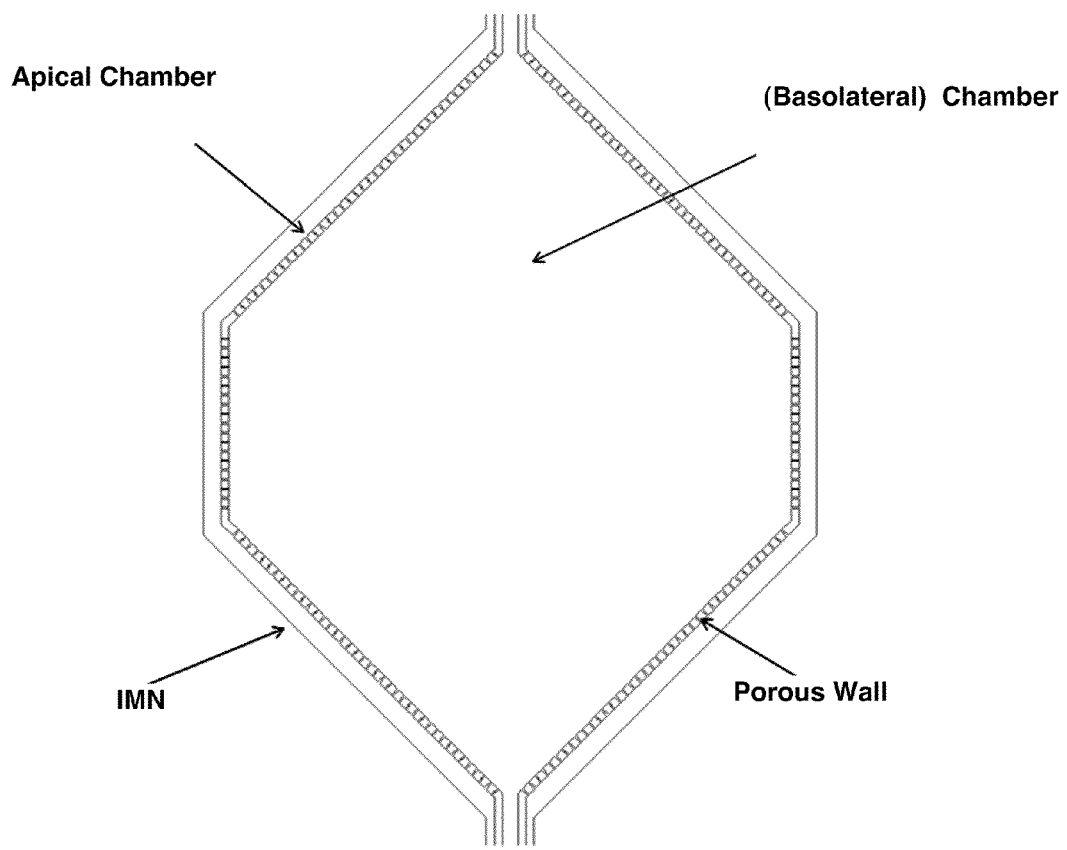
FIG. 4 is a drawing showing an IMN on a microfluidic chip.
Figure 5:
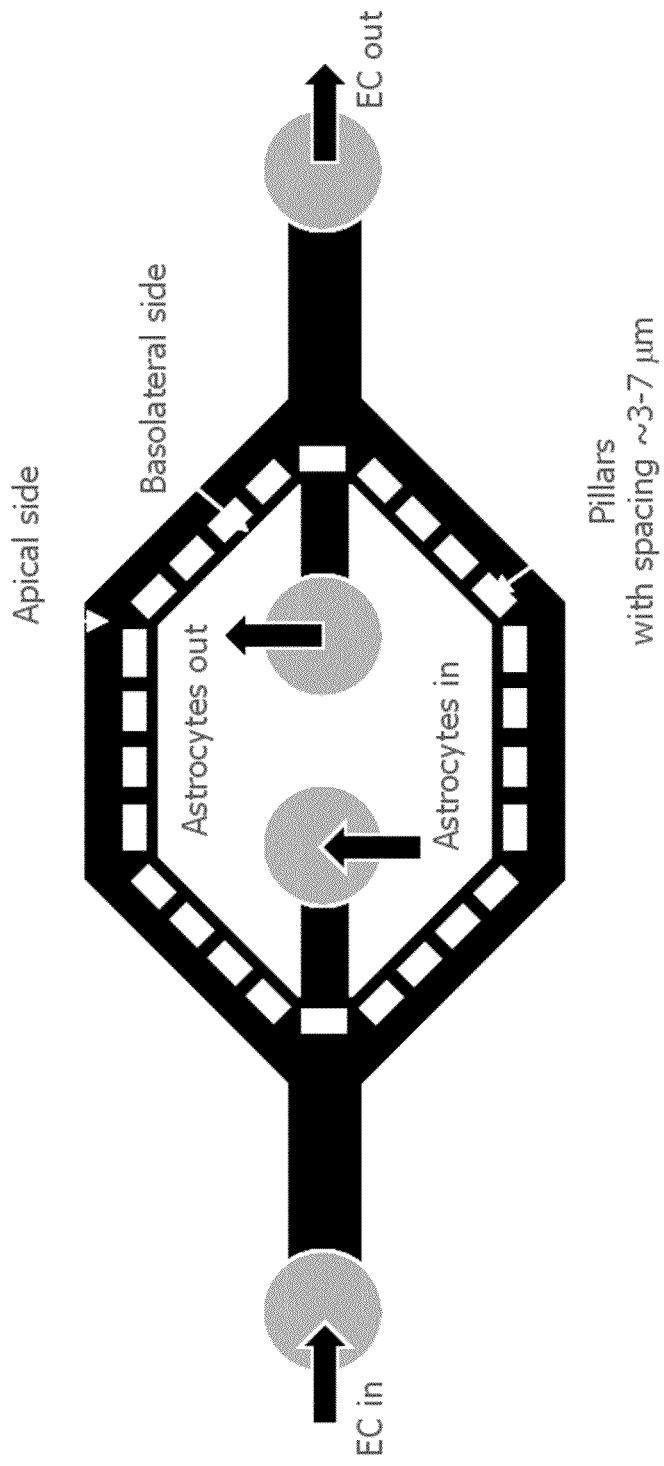
FIG. 5 is a drawing showing an IMN on a microfluidic chip with endothelial cells on the apical (vascular) chamber and astrocytes on the basolateral (tissue) chamber with fluidic paths for inlet and outlet of corresponding media/buffers, solutions, etc.
Figure 6:
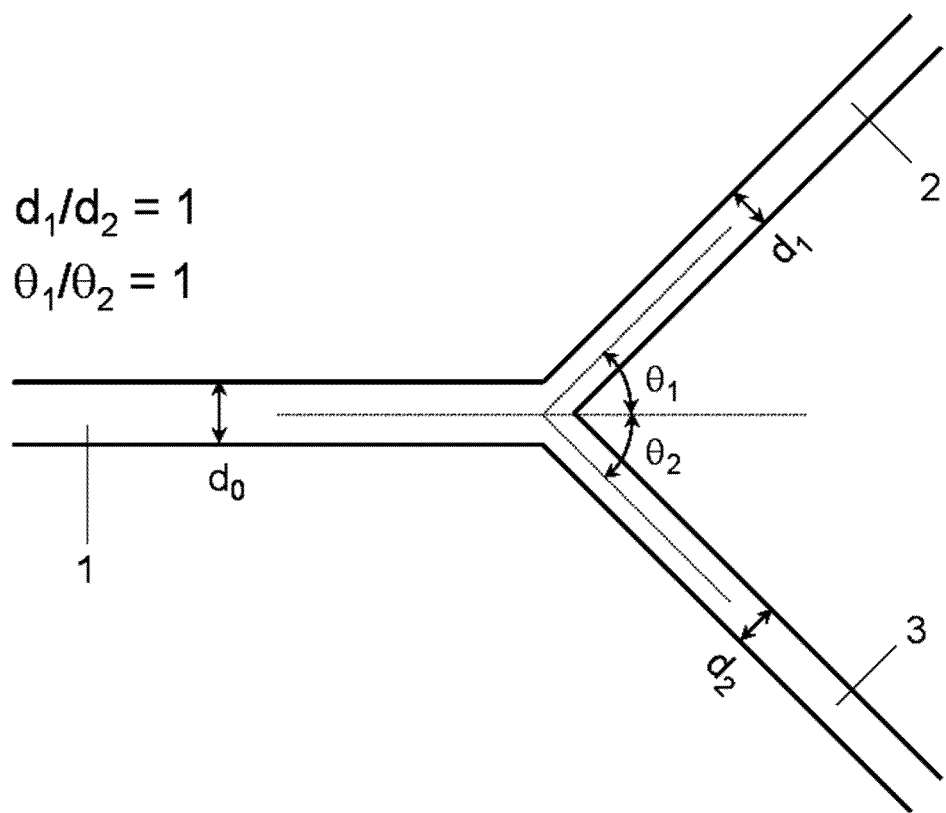
FIG. 6 shows a symmetric bifurcation with symmetric daughter diameters.
Figure 7:
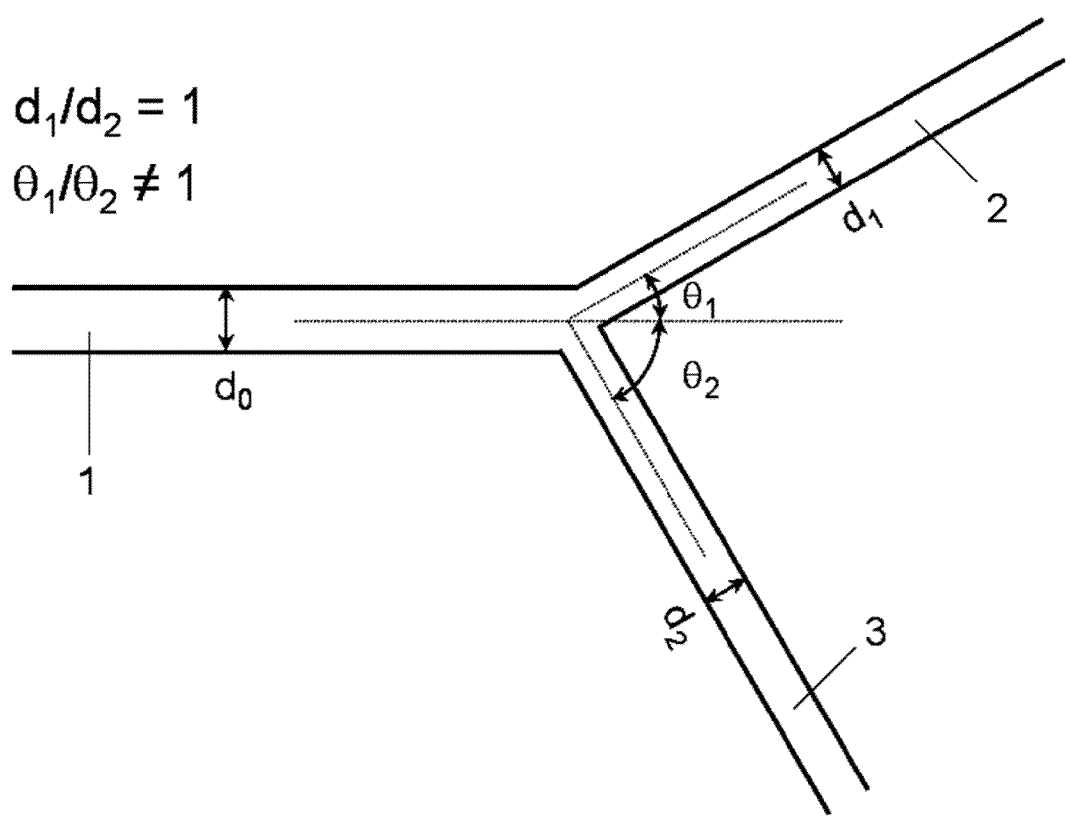
FIG. 7 shows an asymmetric bifurcation with symmetric daughter diameters.
Figure 8:
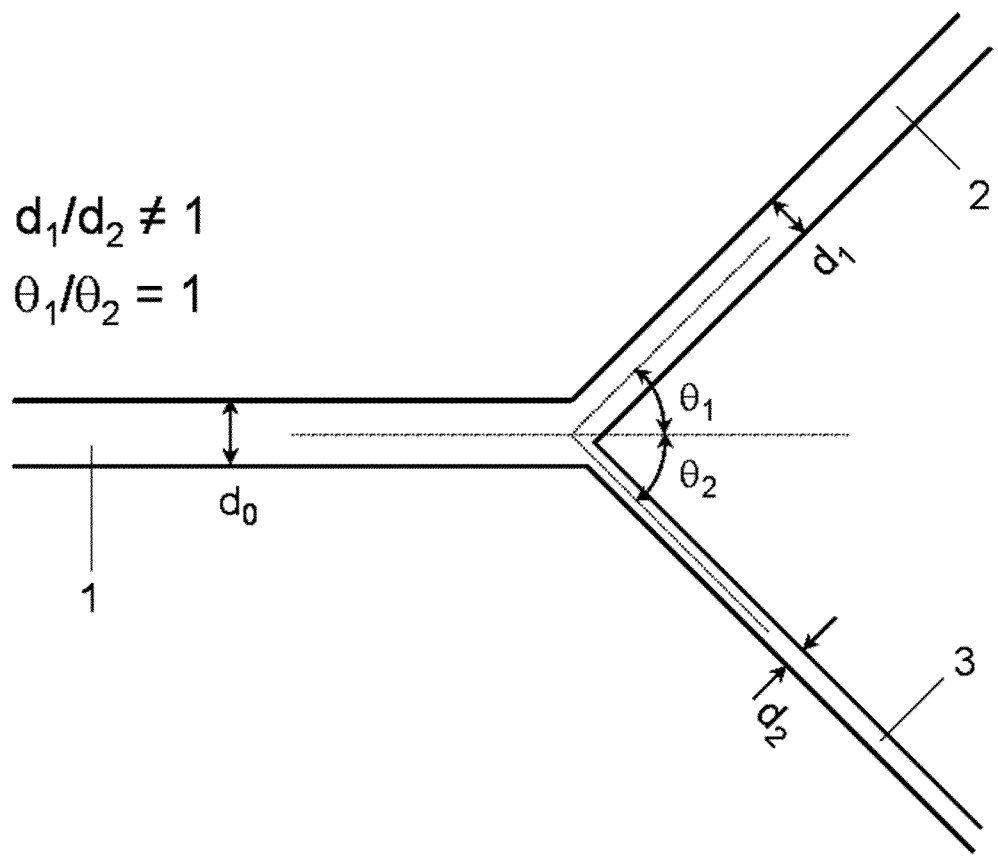
FIG. 8 shows a symmetric bifurcation with asymmetric daughter diameters.
Figure 9:
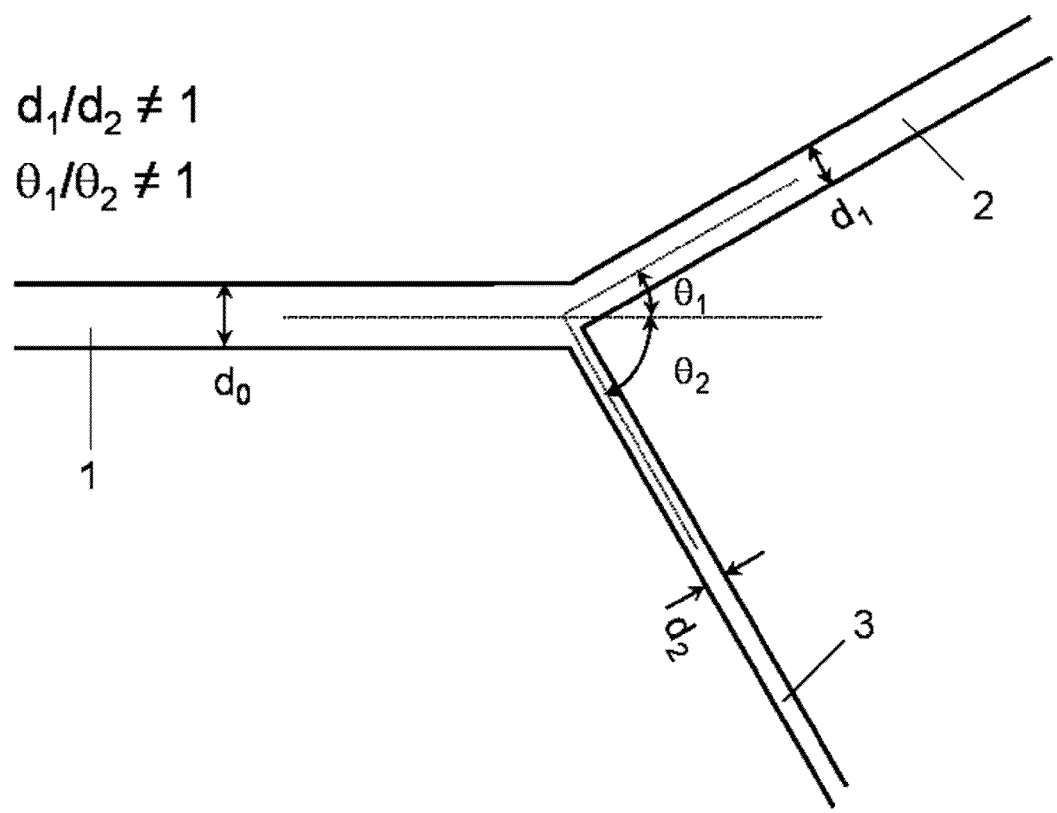
FIG. 9 shows an asymmetric bifurcation with asymmetric daughter diameters.

FIG. 4 shows a portion of an IMN in a microfluidic chip. In this example, a tissue space is surrounded by linear flow channels. The walls separating the tissue space from the flow channels are permeable to aqueous buffers and are formed by plastic structures separated by gaps that range in size from 0.2 µm to 5 µm. Alternatively, the walls may be made liquid permeable by way of pores that are from 0.2 µm to 5 µm FIG. 5 shows a particular embodiment of an IMN comprising a tissue space that contains an apical chamber inlet/outlet and a basolateral chamber inlet/outlet. In this embodiment, a suspension of astrocytes flows through the tissue space to support the growth and function of brain endothelial cells growing on the apical side of the liquid permeable walls. The flow channels are between 10 µm and 500 µm wide and between 10 µm and 500 µm deep. The liquid permeable wall separating the tissue space from the lumen of the flow channels comprises posts that functionally mimic the use of membranes in conventional assays. Brain endothelial cells are grown on the apical side and glial cells are grown on the basolateral side facing the tissue space lumen. Astrocyte conditioned media or a suspension of astrocytes flows though the tissue space lumen. Gaps between posts allow communication between the flow channels and the tissue space. Flow rates designed to replicate typical shear rates encountered in the brain microcirculation are used within the flow channels.

Obtaining Geometries for SMNs:

The geometries for SMNs are derived from physiological microvascular networks. A geometry may, for example, be an exact replica of a digitized image of a natural microvascular network or an average of several digitized images. Maps of complete microvascular networks are constructed from a collage of arterioles, capillaries and venules. An entire network is digitized by tracing each vessel on the assembled collage in AutoCad Map® using a computerized drawing board such as Drawing Board III®, CalComp.

After a network is digitized, an AutoCad Map® cleanup routine is used to ensure all vessels are properly connected at their common nodes. A tolerance value is set which distinguishes between common nodes and neighboring end points. Each vessel is graphically represented by a polyline consisting of a series of straight lines connected through vertices. The routine compares the distances between successive vertices in a polyline to the set tolerance value. A vertex is removed from the polyline if the distance is below the set tolerance value. Brain microvascular structures can be obtained using intra-vital microscopy techniques and animal models, such as open brain model in rodents. Additional methods of imaging brain microvasculature include digital photographs of brain microvascular networks or reconstruction of harvested brain tissue using confocal microscopy.

Reconstructed "Averaged" Microvascular Networks:

Averaged or nominal micovascular networks are based on the geometries of at least two actual physiological microvascular networks. The images are analyzed as described above and subjected to a detailed morphological analysis to yield statistical data of morphometric parameters such as ratios of parent to daughter vessel diameters, branching angles, distances between branches, ratios of branch length to branch channel diameter, tortuosity, bifurcation branch density, and recombining branch density. Averaged microvascular networks can be generated by using averaged morphometric data and/or stochastic sampling of probability density functions for morphometric data. Averaged microvascular networks may be generated using values selected from a variety of statistical distributions for individual morphometric parameters. The values used need not be "average," "mean," or "median" values for measured morphometric parameters.

Idealized Microvascular Networks (IMNs)

Idealized microvascular networks comprise single or multiple bifurcations and/or junctions consisting of linear parent and daughter channels having rectangular or circular or semi-circular cross-sections that diverge or converge at angles of between 15° and 135°. The diameters or cross-sections of the channels are between 10 µm and 500 µm. The bifurcations and junctions are categorized as illustrated in FIG. 6 through FIG. 9. In the figures, $d_0$, $d_1$, and $d_2$ represent the diameters of the parent (1) and first and second daughter channels (2, 3), respectively. $\theta_1$, and $\theta_2$ represent the angles formed between the parent channel (1) and the first and second daughter channels (2, 3), respectively. "Diameter" in the context of channels having a rectangular cross-section refers to the longest cross-sectional distance and cross-sectional area is calculated as width×depth. For channels having circular cross-sections, cross-sectional area is calculated as diameter×diameter×π/4. For channels having semi-circular cross-sections, "diameter" refers to the longest cross-sectional dimension and cross-sectional area is calculated as diameter×diameter×π/8.

Microfluidic Chip Fabrication:

Microvascular network structures obtained from in vivo animal data as for SMN or averaged or IMN are patterned onto an optically clear plastic such as PDMS (polydimethylsiloxane) using conventional soft lithography/replica casting techniques and as described in U.S. Ser. No. 11/393,715. CAD drawings of physiological networks are modified to include gaps in the walls of the vessels. The patterns of these vessels include tissue sections including selected locations ranging from one to the entire tissue space comprising wall sections with gaps with dimensions between 0.2 µm to 5 µm. The flow channels may be covered with extracellular matrix components such as fibronectin, collagen, integrins, and other proteins and proteoglycans. A similar approach may be used to fabricate the IMN with gaps having dimensions between 0.2 µm and 5 µm.

Culture of Endothelial Cells and Astrocytes:

Sterile phosphate buffer saline is injected into a SMN or an IMN at a flow rate of 10 µl/min for 10 minutes using a syringe pump to prime the device. Extracelluar matrix (e.g., fibronectin, gelatin, collagen) at a concentration of 50 µg/ml and flow rate of 10 µl/min is introduced into the apical chamber for 5 minutes. Flow is stopped and matrix solution is allowed to incubate for 2 hrs at room temperature to completely saturate the surfaces. Brain endothelial cells (primary or immortalized) at a concentration of $5 \times 10^3$ to $5 \times 10^7$ cells/ml are introduced into the chamber with media and allowed to incubate for 4 hours. Media is replaced every 24 hours until the cells are confluent (>80%) in the network.

The basolateral chamber is coated with basement membrane matrix such as collagen, lysine, matrigel. Astrocytes, glial or other neuronal cells (primary and immortalized) at a concentration of $5 \times 10^3$ to $5 \times 10^7$ are injected into the chamber and allowed to incubate for 4 hours. Media is replaced every 24 hours until the cells are confluent (>80%) in the network. Instead of cells, the basolateral chamber can also be filled with astrocyte conditioned media (ACM, media taken from astrocyte cell culture) for creation of the SyM-BBB.

Figure 10:
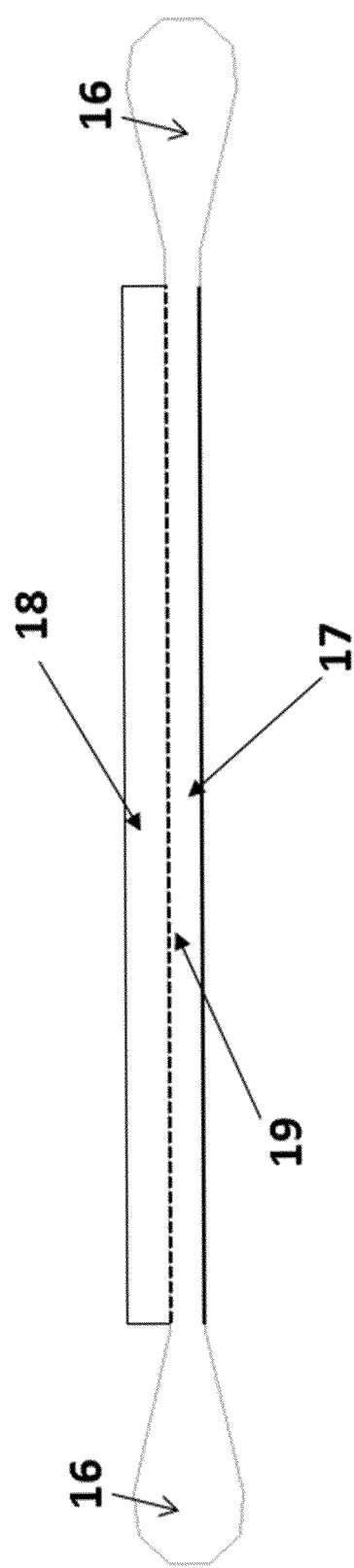
FIG. 10 shows a simplest embodiment of a microfluidic chip for a blood-brain barrier penetration assay.

Various additional embodiments of the SyM-BBB are also envisioned. For example, the separating structures may be posts having various cross-sectional shapes (e.g., diamond, circular, square). Rather than employing entire sections of the microvasculature or even simple bifurcations, a most simple idealized realization comprises of two channels (FIG. 10), in which a first channel serves as a flow channel and a second serves as a tissue space. The two channels are separated by a liquid permeable gap corresponding to the liquid permeable gaps between flow channels of a SMN or an IMN and a tissue space.

Also, by bonding the polymer microchannel of a PDMS microchip to a custom glass bottom laid out in the appropriate form, the microchip may also be realized in a format compatible with standard 24 or 96 well plates, providing a ready method to scale-up to high-throughput screening. Another advantage of the invention is the ability to study differences in BBB penetration between healthy and diseased cerebral microvasculature by changing endothelial cell, glial cell, and/or astrocyte morphology and/or perfusion conditions such as shear rate and flow velocity of the network.

Figure 11:
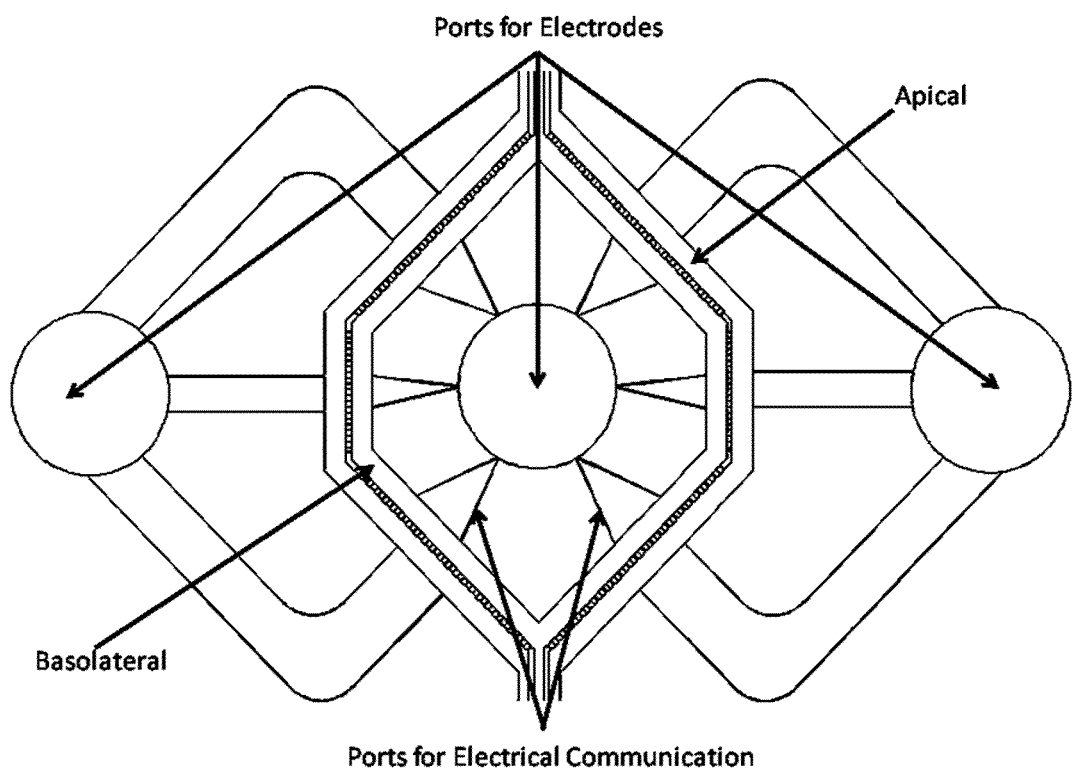
FIG. 11 shows an IMN with ports for electrode insertion for measurement of electrical impedance.

Measurement of Tight-Junctions in the BBB Using Electrical Means:

Trans-endothelial electrical resistance (TEER) provides a measure of the formation of tight-junctions in the synthetic BBB. The technique employs an electrical circuit with the endothelium positioned as a variable resistor. Ag/AgCl apical and basal electrodes are inserted in their respective intake ports as indicated in FIG. 11, sandwiching the BBB between these electrodes. Both analytic and reference currents are pulsed across the cell. The difference between the reference and analytic currents can be used to compute the resistivity of the BBB. Measurements can also be made using alternating current (AC) fields to obtain the complex impedance of the BBB.

Measurement of Tight-Junctions in the BBB Using Biochemical Means:

The endothelial cells cultured on the apical chamber start expressing certain proteins that are indicative of the formation of tight junctions. Common examples are occluding; ZO-1, and claudin 1 and 5 and P-glycoprotein. Endothelial cells grown to confluence in the apical chamber in presence of astrocytes or ACM are harvested and subjected to Western blot analysis for quantitation of the protein expression levels.

BBB Penetration and Screening of Drugs and Drug Delivery Vehicles:

Standard compounds that have been shown to be impermeable to the BBB are used to verify the integrity of the SyM-BBB. The integrity of the blood-brain barrier may be assessed by monitoring the formation of tight-junctions between endothelial cells. The presence of well-differentiated tight junctions may be monitored by parallel permeability measurements of FITC-Dextran. Concentrations of test compounds are varied to measure the affect of concentration vs. permeability. The perfusion rate is varied to provide a range of shear rate from $1\text{-}2000\ s^{-1}$ to measure the effect of flow rate upon BBB penetration.

Fluorescently tagged drug or drug delivery vehicle of a predetermined concentration is introduced into the inlet of the apical side at the desired shear rate ($1\text{-}2000\ sec^{-1}$) using a peristaltic pump or a syringe pump. The apical and basolateral sides are imaged continuously to measure the fluorescent intensity in the basolateral chamber of the device. A higher intensity correlates with more efficient transport through the BBB. Degradation of the drug or drug delivery vehicle is monitored in the flow channels by measuring loss of intensity in the apical chamber. Concentrations of the drug or drug delivery vehicle and shear rate are varied to determine the affects of concentration and shear rates on stability, aggregation, and BBB penetration. The experiment is optionally repeated with the drug or drug delivery vehicle suspended in whole blood, apheresed blood, and in media containing white blood cells, red blood cells and/or platelets.

Complex flow in the device may be characterized experimentally or using computational fluid dynamics (CFD) simulations in advance of the assay and stored in a database. The experiment may be repeated using flow rates corresponding to different shear rates or the device can be designed to incorporate regions providing different shear rates at the same flow rate at the inlet or inlets to allow data collection at varying shear rates.

The invention claimed is:

1. A method for measuring the ability of a drug or drug delivery vehicle to cross a blood-brain barrier comprising the steps of:
   a) introducing a liquid containing the drug or drug delivery vehicle into a network inlet of an optically transparent plastic microfluidic chip, said microfluidic chip comprising:
   a network of interconnected flow channels in liquid communication with a network inlet and a network outlet, said flow channels having luminal cross-sectional dimensions of between 10 μm and 500 μm and a tissue space in liquid communication with a tissue space inlet and a tissue space outlet, said tissue space having cross-sectional luminal dimensions of between 100 μm and 1 cm wherein:
   the tissue space is separated from a lumen of at least one flow channel by a liquid permeable wall and is in liquid communication with the at least one flow channel through said liquid permeable wall;
   the luminal surfaces of the flow channels are coated with endothelial cells; and
   the luminal surfaces of the tissue space contains brain cells and/or cell growth media;
   b) causing the liquid containing the drug or drug delivery vehicle to move though the network of interconnected flow channels; and
   c) quantifying the amount of the drug or drug delivery vehicle reaching the tissue space.

2. The method of claim 1, wherein the surface of the flow channels or the tissue space are coated with a substance selected from the group consisting of a gel, a basement matrix, an extracellular matrix, a tissue matrix, a synthetic matrix, a natural matrix and combinations thereof.

3. The method of claim 1, wherein a surface of the tissue space is coated with glial cells, astrocytes, neurons or combinations thereof.

4. The method of claim 1, wherein the tissue space contains astrocyte-conditioned media, neural cell-conditioned media, glial cell-conditioned media or combinations thereof.

5. The method of claim 1, wherein a surface of the flow channels is coated with endothelial cells (primary or immortalized) originating from brain vasculature.

6. The method of claim 1, wherein quantifying the amount of the drug or drug delivery vehicle is performed by a means comprising optical, electrical, chemical or biochemical detection.

7. The method of claim 1, wherein formation of tight junctions by cells in the interconnected flow channels and/or tissue space is evaluated using electrical, optical, chemical or biochemical means.

8. The method of claim 1, wherein the liquid containing a drug or drug delivery vehicle is moved through the network of interconnected flow channels once, multiple times, or is recirculated through the network of interconnected flow channels using electrokinetic forces, pumps and/or other pumping mechanisms.

9. The method of claim 1, wherein a liquid containing a plurality of drugs or drug delivery vehicles is introduced into the network inlet in step a).

10. The method of claim 1, and further comprising the method step of measuring a property of the drug or drug delivery vehicle, said property selected from the group consisting of: real-time circulation, stability, half life, rate of aggregation, rate of degradation and combinations thereof.

11. The method of claim 1, wherein the drug delivery vehicle or drug is selected from the group consisting of: a cell, a liposome, a lipisome, a lipoprotein, a microencapsulated drug, a particulate drug carrier, a nanoparticle, a microparticle, a nanocrystal, a polymer bead, a virus, a bacterium, a naturally occurring protein, a synthetic protein, a naturally occurring compound, a synthetic compound, and combinations thereof.

12. The method of claim 11, wherein quantifying the amount of the drug or drug delivery vehicle reaching the tissue space measurement is performed while fluid is moving within the network or under static fluidic conditions.

13. The method of claim 1, wherein the liquid is moved through the network of interconnected flow channels with varying fluidic shear rate values of between 1 $\sec^{-1}$ and 2000 $\sec^{-1}$, as measured experimentally or predicted by computational simulation.

14. The method of claim 1, wherein the liquid is selected from the group consisting of: a cell culture media, a buffer containing serum proteins, whole blood, apheresed blood, a buffer containing leukocytes, a buffer containing erythrocytes, a buffer containing platelets, and combinations thereof.

15. The method of claim 1, wherein said network of interconnected flow channels is a synthetic microvascular network or an idealized microvascular network.

16. The method of claim 1, wherein said liquid permeable wall comprises impermeable structures separated by a gap distance.

17. The method of claim 16, wherein said gap distance is between 0.2 µm and 5 µm.

18. The method of claim 16, wherein the gaps are filled with a substance selected from the group consisting of a gel, a basement matrix, an extracellular matrix, a tissue matrix, a synthetic matrix, a natural matrix and combinations thereof.

19. An optically transparent microfluidic chip comprising:
   a) a network of interconnected flow channels in liquid communication with a network inlet and a network outlet, said flow channels having luminal cross-sectional dimensions of between 10 µm and 500 µm and
   b) a tissue space in liquid communication with a tissue space inlet and a tissue space outlet, said tissue space having cross-sectional luminal dimensions of between 100 µm and 1 cm wherein:
   the tissue space is separated from a lumen of at least one flow channel by a liquid permeable wall and is in liquid communication with said flow channel through said liquid permeable wall;
   the luminal surfaces of the flow channels are coated with endothelial cells; and
   the luminal surfaces of the tissue space contains brain cells and/or cell growth media.

20. The microfluidic chip of claim 19, wherein the network of interconnected flow channels is a synthetic microvascular network or an idealized microvascular network.

21. The microfluidic chip of claim 19, wherein the geometry of the synthetic microvascular is identical to a digitized physiological microvascular network or an average of two or more digitized physiological microvascular networks.

22. The microfluidic chip of claim 19, wherein the network of interconnected flow channels comprise bifurcation angles of between 15 and 135°.

23. The microfluidic chip of claim 19, wherein the network of interconnected flow channels is an idealized microvascular network comprising flow channels having asymmetric and/or symmetric branches and cross-sections.

24. The microfluidic chip of claim 19, wherein the liquid permeable wall comprises structures separated by a gap distance between 0.2 µm and 5 µm.

25. The microfluidic chip of claim 24, wherein a surface of the flow channels or the tissue space are coated with or the gaps are filled with a substance selected from the group consisting of a gel, a basement matrix, an extracellular matrix, a tissue matrix, a synthetic matrix, a natural matrix and combinations thereof.

26. The microfluidic chip of claim 19, wherein the surface of the flow channels is coated with endothelial cells obtained or derived from the vasculature of a mammalian brain.

27. The microfluidic chip of claim 19, wherein pressures are regulated inside the flow channels and the tissue space.

28. The microfluidic chip of claim 19, wherein the tissue space contains astrocyte conditioned media, neuronal conditioned media, glial conditioned media or a combination thereof.

29. The microfluidic chip of claim 19, wherein a surface of the tissue space is coated with glial cells, astrocytes, neurons, or a combination thereof.

30. An apparatus comprising the microfluidic chip of claim 19;
   means for moving fluid from the network inlet to the network outlet; and
   means for measuring the integrity of an artificial blood-brain barrier comprising said liquid permeable wall and said endothelial cells selected from the group consisting of optical, electrical, chemical and biochemical detection means.

31. An apparatus comprising the microfluidic chip of claim 19;
   pumping means configured to move fluid from the network inlet to the network outlet; and
   means for detecting a drug or drug delivery vehicle in the tissue space selected from the group consisting of optical electrical, chemical and biochemical detection means.

* * * * *